(12) United States Patent
Truong (10) Patent No.: US 10,517,706 B2
(45) Date of Patent: Dec. 31, 2019

(54) PORTABLE AUTOMATIC VETERINARY INJECTOR DEVICE

(71) Applicant: DESVAC, Saint-Barthelemy-d Anjou (FR)

(72) Inventor: Hieu Trong Truong, Hochiminh (VN)

(73) Assignee: DESVAC, Saint-Barthelemy-d Anjou (FR)

( * ) Notice: Subject to any disclaimer, the term of this patent is extended or adjusted under 35 U.S.C. 154(b) by 0 days.

(21) Appl. No.: 15/548,611

(22) PCT Filed: Feb. 4, 2016

(86) PCT No.: PCT/IB2016/000179
§ 371 (c)(1),
(2) Date: Aug. 3, 2017

(87) PCT Pub. No.: WO2016/125016
PCT Pub. Date: Aug. 11, 2016

(65) Prior Publication Data
US 2018/0028298 A1 Feb. 1, 2018

Related U.S. Application Data

(60) Provisional application No. 62/111,759, filed on Feb. 4, 2015.

(51) Int. Cl.
*A61D 7/00* (2006.01)
*A61D 1/02* (2006.01)
*A61B 17/20* (2006.01)

(52) U.S. Cl.
CPC .............. *A61D 7/00* (2013.01); *A61B 17/205* (2013.01); *A61D 1/025* (2013.01)

(58) Field of Classification Search
CPC ....... A61D 7/00; A61M 5/204; A61M 5/3137; A61M 2205/502; A61M 2205/505;
(Continued)

(56) References Cited

U.S. PATENT DOCUMENTS 676,173 A 6/1901 Beese
4,204,539 A 5/1980 Van Brugge
(Continued)

FOREIGN PATENT DOCUMENTS

WO 03/082381 A1 10/2003
WO 2009/120692 A2 10/2009

OTHER PUBLICATIONS

Office Action dated Sep. 5, 2017 in European Patent Application No. 16709561.1.
(Continued)

*Primary Examiner* — Bhisma Mehta
*Assistant Examiner* — Nidah M Hussain
(74) *Attorney, Agent, or Firm* — Oblon, McClelland, Maier & Neustadt, L.L.P.

(57) ABSTRACT

An injector device for veterinary use, such as to inject vaccine into the chicken breast muscle. The device includes a finger-held unit connected to a vaccine pumping main unit using a flexible conduit. The operator can quickly start an injection by stroking alongside the breast edge of a grasped chicken, using his fingertips to touch and select the muscle, then start an injection by pressing the finger-held unit against the chicken breast in a designated way. The electric buttons in the finger-held unit may activate a process that actuates a mechanism to inject a hypodermic needle into the chicken's muscle, the pumping system may-then be actuated to pump the vaccine into the muscle through the injected needle.

9 Claims, 7 Drawing Sheets

(58) Field of Classification Search
CPC .... A61M 5/158; A61M 5/3287; A61M 5/425; A61M 2005/1586; A61B 5/6885; A01K 45/007; A01K 13/003
See application file for complete search history.

(56) References Cited

U.S. PATENT DOCUMENTS

| | | | |
|---|---|---|---|
| 2002/0188470 A1 | 12/2002 | Hogan | |
| 2009/0018505 A1* | 1/2009 | Arguedas | A61D 1/025 604/131 |
| 2010/0016796 A1 | 1/2010 | Derichs | |
| 2011/0152838 A1* | 6/2011 | Xia | A61M 11/06 604/514 |
| 2012/0203095 A1* | 8/2012 | Krieger | A61B 5/055 600/411 |
| 2016/0324613 A1* | 11/2016 | Halamish | A61D 1/025 |

OTHER PUBLICATIONS

International Search Report dated May 18, 2016, in PCT/IB2016/000179, filed Feb. 4, 2016.

* cited by examiner

PORTABLE AUTOMATIC VETERINARY INJECTOR DEVICE

BACKGROUND OF THE INVENTION

Field of the Invention

The present invention relates to the field of injectors for dispensing veterinary products into an animal, more particularly, the present invention relates to devices for intramuscular vaccine injections for animals such as layer chickens to the breast muscle.

Description of the Related Art

Vaccination programs cost a lot of labor time in today's poultry industry. In particular, the time used for the vaccination program for layer chickens does not only need more labor costs, but also limits the flexibility of vaccination programs in large size farms.

Traditional vaccination methods such as water drinking, exposes many limitations: not all the chickens drink the full dose of vaccine solution, even after hours of water deprivation, especially in cold temperatures. The live vaccines used in water drinking method can only protect a limited number of diseases, for limited period of the chickens' lifetime in the poultry industry today.

In-Ovo injection technology (U.S. Pat. No. 6,032,612 A to Williams) or Day-Old Chick injection technology (U.S. Pat. No. 3,964,481 to Gourlandt et al.) discloses devices providing each embryo or new born chick with a full dose of vaccine. Despite this method being widely used in the world, it can only be used for a few vaccines such as Marek and Newcastle Disease.

Intramuscular injecting in the chicken breast at a premature age is the only vaccination method against some diseases, especially for layer chickens which have a long life laying eggs and need full protection from many diseases. In floor farms where layer chickens are raised together in the thousands, to inject the chicken in the breast muscles, the vaccinator captures the birds and keeps them still by holding their legs and/or wings, the vaccinator then injects them with a handheld syringe. The chickens are then released into a separated area to separate them from the unvaccinated ones. In another method, the assistant will pass the captured chickens to the vaccinator and the vaccinator will keep them still with one hand, inject them with the other hand and then release them into the separated area. With both methods, one vaccinator needs at least one assistant to support the vaccination process.

Despite most of the handheld syringes being refilled after each injection, the vaccinators became easily tired after thousands of shots. Moreover, because the injection site and the distance the needle to be inserted into the chick is determined by eye, tired operators working in a low light conditions tend to inject the birds at the wrong sites, where the muscles are too thick or too thin for the vaccine. The tired vaccinators may also inject the needle at a wrong depth into the muscle, too deep or too shallow, these mistakes may seriously harm the chickens' organs, leaving the birds unprotected or even killing the bird after the injection. They sometimes inadvertently inject themselves, which can cause serious pain. To overcome the problems associated with manual vaccination methods, some devices have been developed to support intramuscular vaccination.

U.S. Pat. No. 4,758,227 to Lancaster Jr. et al. and U.S. Pat. No. 8,211,058 to Jorna et al. disclose methods to vaccinate intramuscular layer chickens in their breast muscles. Both inventions provide automatic injection devices where the chickens automatically inject when they are placed in the proper position on the machines sites. The machines save man power of injecting and pumping the handheld syringes, but they need many workers to operate. Normally, at least three workers are needed to operate one machine. The operator(s) push the chicken to the machine at the proper position and/or direction, wait for the injection to be completed then drop the vaccinated chickens to a separated area. One machine operator needs at least two assistants to help him capture the birds. The large embodiments of the two machines also make them hard to be moved around in a chicken house, or house to house within a farm.

U.S. Pat. No. 6,858,020 B2 to Rusnak provides a portable automatic injector that can be moved around the farm easily. The device comprises one handheld needle assembly which is connected to an automatic syringe located on the floor. The device saves man power to pump the syringe, but the operators still need to select the injection site by eye, injects the needle and activate the syringe to pump the vaccine manually.

In more particular conditions when the chickens start to lay eggs and they are moved to cages, taking the chickens out of their cages to vaccinate costs a lot of labor time, causes the chickens stress and may even physically harm them. Normally a large number of caged chickens break their wing bones after being vaccinated. To avoid taking the birds out of their cages, an alternative intramuscular method is to inject their legs. Operators pull the chicken leg out of the cage doors and inject in the leg muscles, this method is risky to the bird's legs, a significant percentage of chicken found to be lame after the vaccination. In conclusion, there is no safe method to vaccinate layer chickens in cages, difficulties with caged chicken vaccination make the farm owners postpone moving their young chickens from floor farms to cage farms until the injection program is complete.

In the layer poultry industry, young layer chickens need to be vaccinated by the intramuscular method many times to protect against various diseases. Current methods to perform breast intramuscular vaccination has many limitations: high cost of labor, unsafe to the chickens' health, especially for the chickens raised in cages, and even unsafe to the vaccinator. An invention related to a device to be chicken breast intramuscular vaccination speed and safety, providing convenience to operate and move around, can overcome these limitations and provide farm owners more choices of scheduling of vaccination program, planning for moving flocks and thus bring better performance profit.

SUMMARY OF THE INVENTION

A portable automatic veterinary injector device is disclosed which is configured to dispense veterinary products into an animal. In some embodiments, the device may be configured to dispense intramuscular vaccine injections for layer chickens to the breast muscle. In further embodiments, the device may comprise a finger-held unit that can be attached firmly on the operator's fingers connected to a main unit which may be carried on the operator's body through flexible wires and tubes. The operator may use the fingers and palm to select the best site on the chicken's body and then activate the injection by pressing the finger-held unit against the chicken's breast. The pressed pushbuttons on the finger-held unit may send the closed-circuit signal to the main unit, the main unit may then activate the injecting mechanism in the finger-held unit to inject a hypodermic needle into the chicken's muscle using a linear actuator on the finger-held unit. The actuator may gain the power from compressed air provided from the main unit, which may be activated by a solenoid valve on the finger-held unit or main unit. The angle of the needle to the muscle surface and the depth the needle in fully injected state may be adjustable and can be fixed by locking nuts and knuckle, joints or other suitable method. In further embodiments, the signal occurs when the needle is completely injected into the chicken breast muscle to its preset length, which may be detected by the ti or piston position detector, activates the main unit to pump a full dose of vaccine into the chicken's muscle via a flexible tube connected to the needle. The syringe to pump the vaccine in the main unit may be actuated by a linear actuator, which may gain power from an external compressed air source. The event when a full dose of vaccine is completely pumped, which may be detected by a piston position detector, may activate the controller to withdraw both the injecting mechanism and the pumping mechanism and sets the whole system in an inactive state waiting for a new injection process. The withdrawal of the pumping mechanism may also fill the syringe with a new dose of vaccine for a subsequent injection.

The hand-touch detection of the muscle site to be injected provides a quickly manipulation to start an injection without aiming, while the compressed air power free the manpower from injecting and pumping vaccines to the chickens' muscle. The light bodyweight of the device provides convenience for the operator to carry around the farm.

In a further embodiment of the finger-held unit, the linear actuator may be replaced by a Bowden cable which gains the power of the actuator on the main unit. This embodiment can reduce the space and the weight of the finger-held unit.

In a further embodiment of the finger-held unit, pushbuttons may be replaced by other types of detector or sensor such as pressure sensors, infrared detectors to send activation signals to the main unit. As the size of the chickens within one flock may not be the same, a different level of force from the manipulation of the operator hand may activate the main unit in different levels, which may cause the needle to inject into the chicken breast in different depth.

In another further embodiment, the injecting mechanism and pumping mechanism may gain power from electrical actuator provided from an attached battery pack. This embodiment frees the device from external compressed air tube, providing more convenience for the operator to carry around. The electrical actuators may also provide a flexible movement which may be controlled by a firmware program, which may change the dosing settings and needles length settings by a firmware program.

In a further embodiment, the solenoid valve to drive the actuator on the finger-held unit may be placed on the main unit or on the flexible conduit. Keeping the solenoid valve away from the finger-held unit may reduce the space and the weight of the finger-held unit and reduce the number of wires required to connect the finger-held unit to the main unit.

A firmware algorithm processed by the microcontroller in the controller in the main unit may filter the electric signals from the pressed pushbuttons and may only activates an injection when a valid signal is detected. In some embodiments, the operator has to push the pushbuttons in a conventional method in a predetermined order and/or with timing rules to activate an injection. The algorithm protects both the chickens and the operators from the unwanted injections.

A relief valve may be connected closely to the needle on the finger-held unit to prevent leakage of the vaccine from the needle tip. The relief valve may block the vaccine flow when the syringe is inactive and allows pressurized vaccine when it is pumped from the syringe to go through to the needle.

BRIEF DESCRIPTION OF THE DRAWINGS

The following drawings semi-schematically illustrate the initial and current embodiment of the invention.

DETAILED DESCRIPTION OF THE PREFERRED EMBODIMENTS

List of Numbered Elements

Figure 1:
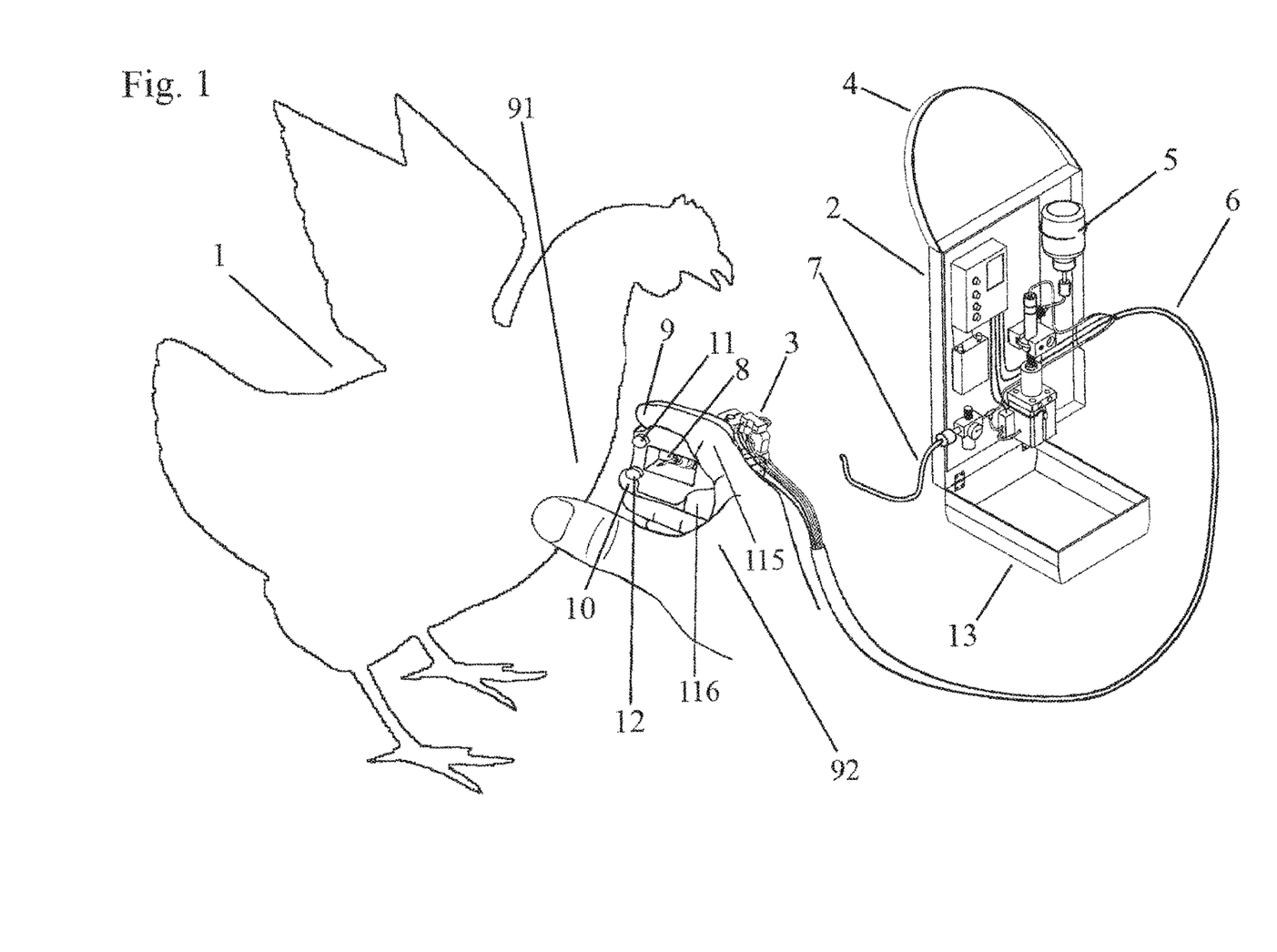
FIG. 1 shows an example of a portable automatic veterinary injector device with the finger-held unit attached to two fingers of a right hand, on the movement toward a chicken's chest and an example of a main unit with cover open according to various embodiments described herein.
Figure 1A:
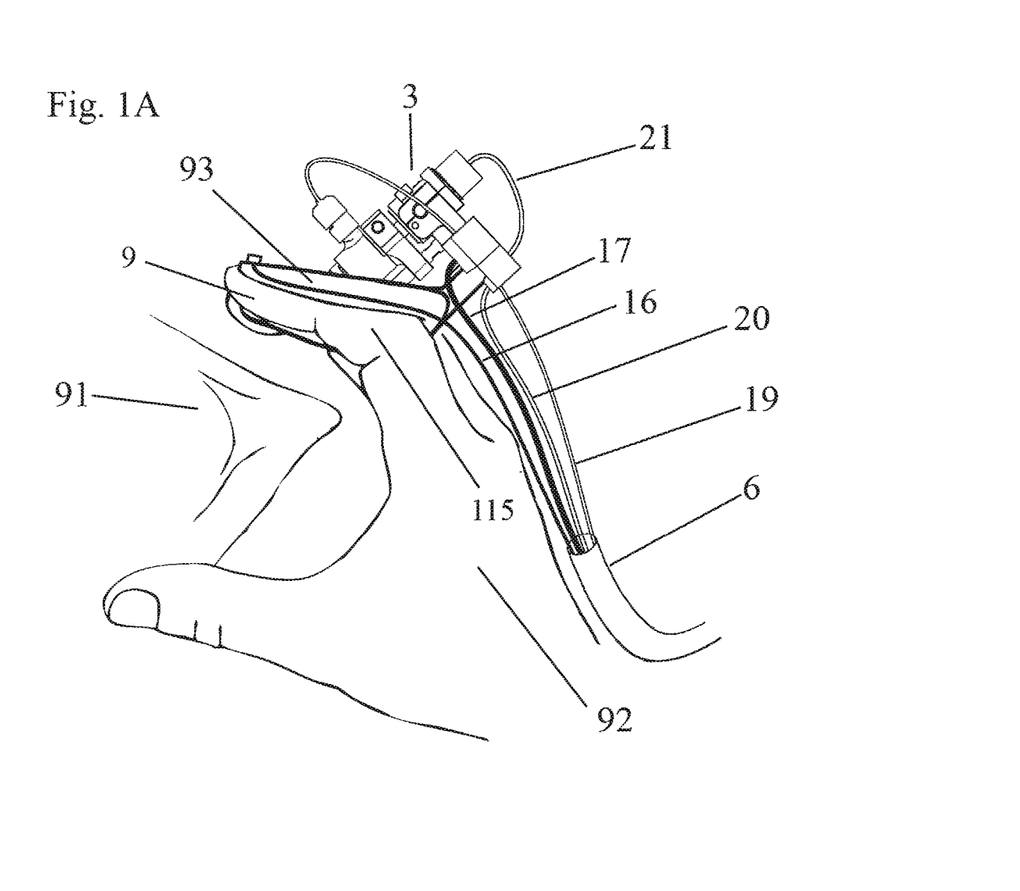
FIG. 1A illustrates a top view of an example of a finger-held unit on the hand of the operator, moving toward the chicken breast according to various embodiments described herein. The Figure provides a closer look on the angle and position of the needle to be injected to the chicken breast.

1 Chicken to be injected
2 Main unit
3 Finger-held unit
4 Hanging belt
5 Reservoir
6 Flexible conduit
7 Compressed air cord
8 Hypodermic needle
9 Index fingertip
10 Middle fingertip
11 Upper push-button
12 Lower push-button
13 Cover
14 Upper push-button cover
15 Lower push-button cover
16 Signal wires
17 Solenoid wire
18 Needle solenoid valve
19 Solenoid tube
20 Needle actuator tube
21 Vaccine tube 22 Relief valve
23 Needle lock
24 Anti-rotating rod
25 Holding nuts
26 Knuckle joint hex screw
27 Needle assembly locking screw
28 Finger bracket
29 Actuator nut
30 Actuator
31 Needle actuator piston
32 Retract spring
33 Piston rod
34 Vaccine inlet
35 Relief valve nut
36 Relief valve spring
37 Actuator holding pad
38 Compress air inlet
39 Anti-rotating ring
40 Guiding rod
41 Vaccine bottle holder
42 Dropping chamber
43 Syringe
44 Vaccine tube—syringe in
45 Syringe actuator
46 Shock absorber
47 Position detector
48 Position detector wire
49 Controller
50 Liquid crystal display (LCD)
51 Buttons
52 Battery pack
53 Syringe solenoid wire
54 Syringe solenoid valve
55 Compressed air tube
56 Compress air divider
57 Compressed air connector
58 Regulator adjusting knob
59 Pressure gauge
60 Water trap
61 Hinges
62 Syringe holder
63 Syringe holder locking nut
64 Syringe locking nut
65 Syringe actuator bracket
66 Frame
67 Panel
68 Stroke locking screw
69 Vaccine inlet port
70 inlet check valve
71 Inlet valve spring
72 Syringe space
73 Syringe piston
74 Actuator brackets
75 Syringe spring
76 Dosing locking nut
77 Syringe piston nut
78 Shock absorber head
79 Shock absorber spring
80 Locking nut
81 Actuator piston
82 Air inlet port
83 Compressed air outlet
84 Actuator spring
85 Outlet check valve
86 Outlet valve spring
87 Vaccine outlet
88 Luer lock
89 Actuator bracket screws
90 Bracket screws to panel
91 Chicken breast
92 Operator's hand
93 Finger-held chassis
94 Needle assembly
95 Syringe piston head
96 Syringe end
98 Startup process
99 Activate needle solenoid Valve
100 Scan lower push-button signal
101 Start Tinier 1
102 Scan lower push-button signal
103 Check Timer 1 expiration
104 Start Timer 2
105 Check Timer 2 expiration
106 Scan upper Push-button signal
107 Start Timer 3
108 Check for Timer 3 expiration
109 Activate syringe solenoid valve
110 Scan for position detector signal
111 Deactivate needle solenoid valve
112 Deactivate syringe solenoid valve
113 Push-buttons signals processing routine
114 Injection routine
115 Operator's index finger
116 Operator's middle finger
117 Arms of chassis
118 Knuckle joint Referring to FIG. 1, in some embodiments, the device may comprise a finger-held unit 3 connected to a main unit 2 carried on the operator's body using a flexible conduit 6. In other embodiments, the main unit 2 may be positioned close to the finger-held unit 3 and the operator's body. The conduit 6 may comprise wires and tubes to transfer signals, power and/or fluid between the finger-held unit 3 and the main unit 2. The chicken 1 to be injected may be grasped at its wings or forced into the cage corner. To start an injection, the operator may move his opened hand 92 carrying the finger-held unit 3 on his fingers toward the chicken's breast 91 with his thumb and palm on one side and the other fingers touching the other side of the chicken breast 91. The best position of the hand 92 shown on FIG. 1A shows that the edge of the breast bone may contact the proximal phalanges of the fingers, the peak of the breast bone may fit into the space between the proximal phalanges of the index finger 115 and the middle finger 116. This position is easy to reach when the operator slides his hand alongside the breast bone edge and the peak position of the bone will reach the space between two the fingers very fast.

In further embodiments, when the breast position is selected, the operator may move his index fingertip 9 and middle fingertip 10 to select the thick muscle of the chicken breast 91, with the thumb on the other side of the chicken's 1 body, he can slightly squeeze the chicken's body with his fingers and the upper push-button and lower push-button may be pressed against the chicken breast muscle, causing a close-circuit state. With the wires connecting the push-buttons to the controller 49 on the main unit 2, the controller 49 may start a process to filter the push-buttons signal to decide if it is a valid activation to start an injection.

Figure 2:
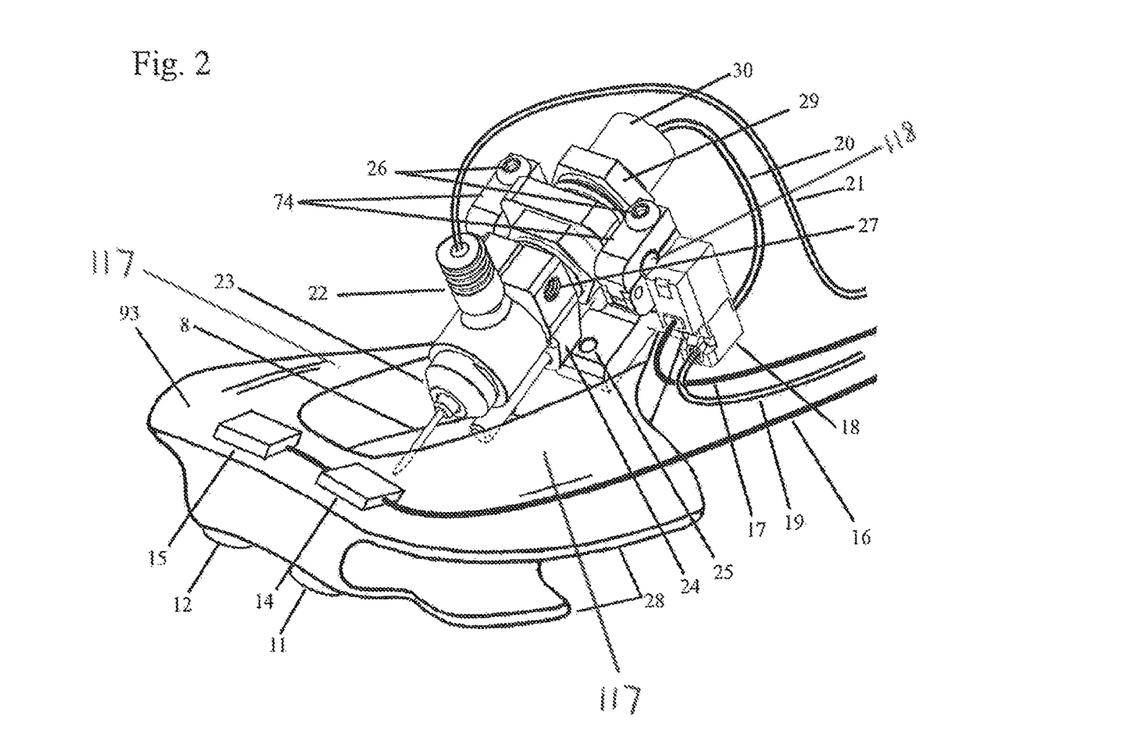
FIG. 2 presents a perspective general view of an example of a finger-held unit according to various embodiments described herein.

FIG. 2 shows the details of the finger-held unit 3, the unit comprises a plastic, metal or other rigid material chassis 93 which may have one slot on each of its sides (or arms 117) that the operator can slot his index finger 115 and middle finger 116 or other desired fingers in. The chassis 93 with arms 117 may form a U-shape. Each slot may have a soft elastic bracket 28 which may be made from silicone, flexible plastic or other elastic and flexible material to firmly embrace the finger, regardless of finger size. The chassis 93 may comprise one or more push-buttons 11 12, button covers 14 15 and the wires to connect the buttons to the main unit 2. The chassis 93 also attaches one or more brackets 74 that hold the actuator 30 and the needle assembly 94 using at least one screw 25. The actuator 30 is configured to move the needle assembly 94 relative to the chassis 93 from a pre-actuated position to an actuated position. The angle between the needle 8 and the injection surface can be adjusted at the knuckle joints 118 locking by the two hex screws 26 or other suitable locking method. The depth of the needle can be adjusted by loosening an actuator nut 29, rotating the actuator 30 body and then locking the nut 29 again or with any other suitable depth selecting method. The angle and depth adjustments allow for adjustment of the orientation and position of the needle assembly relative to the chassis in a pre-actuated position. The adjustable nature of these elements provides a flexible use of the device for various sizes of chickens, pigs, turkeys, ducks, rabbits, or other animals.

Figure 3:
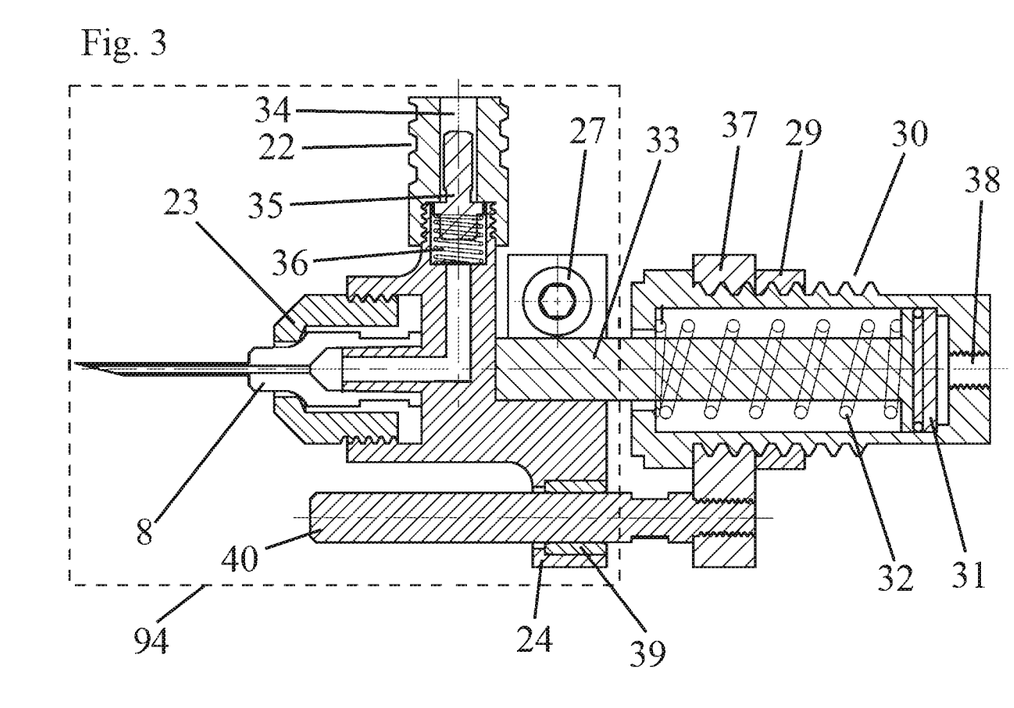
FIG. 3 presents a sectional view of an example of an injection mechanism on the finger-held unit according to various embodiments described herein.

FIG. 3 shows a sectional view of an example of a needle assembly 94 and the actuator 30. After the signals are sent from the pressed push-buttons 11 12 to the controller 49 on the main unit 2 via signal wires 16, the controller 49 may activate the actuator 30 by providing an electric current to the solenoid valve 18 via the solenoid wire 17. The actuated solenoid 18 provides compressed air from the compressed air tube 19 to the actuator 30 via the actuator tube 20. The compressed air goes through the air inlet port 38 and quickly pressurizes the piston 31 surface, pushes the piston 31 to the other side of the port 38 and thus pushes the needle assembly 94 toward the chicken breast 91. The needle assembly 94 may be connected to the piston rod 33 with an embracing arm, fastened by a screw 27 of other connection method. In some embodiments, needle assembly 94 may be prevented from rotating by a guiding rod 40 connected to the actuator by an actuator holding pad 37. A low friction metal ring 39 on an anti-rotating arm 24 may cover the guiding rod 40 and allows the needle assembly 94 to slide linearly without rotation.

When the needle assembly 94 completely moves to the end, which may be determined by a delay time, or by a position detector in another embodiment, the main unit 2 may pump a dose of vaccine to the vaccine inlet 34 on the needle assembly 94 via the vaccine tube 21. The pressurized vaccine goes through the relief valve 22 to the needle and is dispensed to the chicken breast 91 muscle. The strength of the relief valve spring 36 and the surface area of the valve nut 35 may determine the pressure level of the vaccine to get through the relief valve 22. A needle lock 23 may keep the needle 8 attached firmly to the needle assembly 94. When a full dose of vaccine is pumped to the needle 8, which may be determined by a detector on the main unit 2, the controller 49 on the main unit 2 may stop providing an electric current to the solenoid valve 18, and may then stop providing the compressed air to the actuator 30. The retract spring 32 inside the actuator 30 may push the piston 31 back to the normal position, thus pulling the needle 8 out of the chicken breast 91 muscle. The system may then settle to normal status waiting for another injection activation signal.

In an alternative embodiment of the finger-held unit 3, an activation releases a Bowden cable core and releases a compressed spring to push the needle to inject into the chicken's muscle. When a full dose of vaccine is dispensed into the chicken's muscle, the drawn Bowden cable core may pull the needle out of the chicken's muscle and compress the needle spring waiting for next injection. In a further alternative embodiment of the finger-held unit 3, an electric actuator may be used to power the needle to free the device from any external compressed air source.

In an alternative embodiment of finger-held unit 3, another mechanism may be used to replace the locking screw 27 to make the needle assembly 94 easier to be detached from the actuator 30. This mechanism may be used to provide better disinfection methods to the needle assembly 94.

Figure 4:
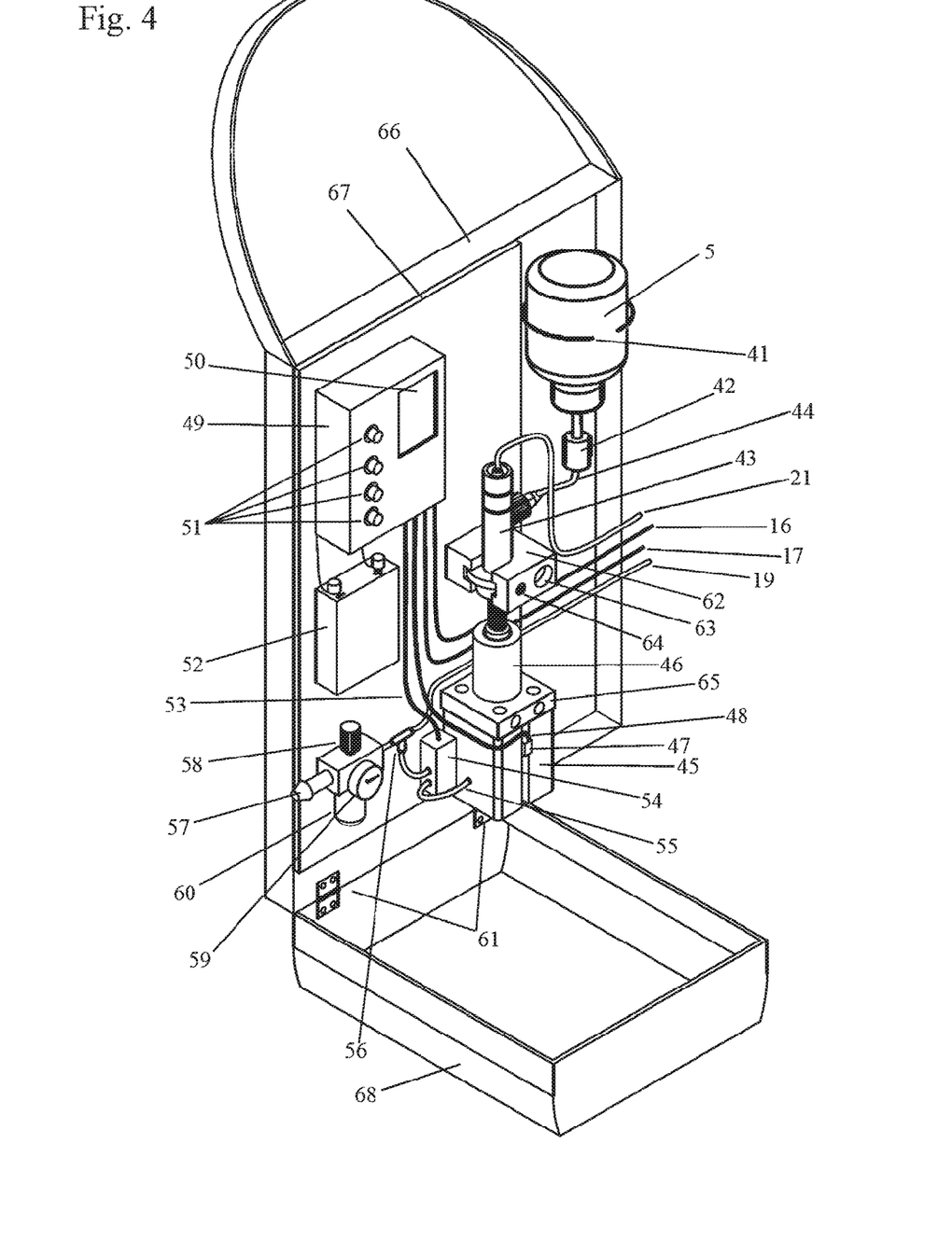
FIG. 4 presents a perspective general view of an example of a main unit according to various embodiments described herein.

FIG. 4 illuminates the details inside an example of a main unit 2. The main unit 2 may be a remote unit. The main unit 2 may comprise an electronic controller 49 powered by a battery pack 52, an actuator powered by an external compressed air source connected through the compressed air cord 7 to the air connector 57 and a syringe 43 which pumps the vaccine from a reservoir 5 to the finger-held unit 3. The elements may be attached to a metal or other rigid material panel 67 which is hard enough to hold the actuator pushing the syringe. A frame 66 holds the panel 67 and the vaccine reservoir holder 41, hung on the operator's shoulder or hip with a belt 4, strap, or the like. A folding cover 13 attached to the panel by one or more hinges 61 may protect the elements of the main unit 2. When closed-circuit signal occurs from push-buttons 11 12 on the finger-held unit 3, a signal may be sent to the controller 49 via signal wires 16, and the controller 49 may start a process to determine the valid signal. When a valid signal is detected, the controller 49 may provide an electric current to the solenoid valve 18 on the finger-held unit 3 via the solenoid wire 17. The controller 49 may then starts a countdown timer to create a delay period for the needle 8 to completely inject into the chicken breast 91. When the delaying process expires, the controller 49 will start a pumping process such as by activating a solenoid valve 54 via the syringe solenoid wire 53. The actuated syringe solenoid valve 54 provides compressed air from the compressed air divider 56 to the syringe actuator 45 via compressed air tube 55. The compressed air pushes the piston 81 of the actuator 45 out, presses the syringe piston 73 of the syringe 43 up and pumps the vaccine inside the syringe 43 to the vaccine tube 21 and then to the finger-held unit 3 to dispense to the chicken breast 91. When the piston 81 of the actuator 45 reaches the end position determined by the position detector 47, the controller 49 may receive the signal from the position detector 47 through the position detector wire 48 and may deactivate the solenoid valve 54 by stops the providing electric current to the syringe solenoid wire 53. The spring 84 inside the actuator 45 pushes the piston 81 back to the normal position and the syringe 43 fills with a full dose of vaccine waiting for another injection. The movement speed of the actuator can be pre-described by adjusting the pressure of the compressed air provided to the actuator. The compressed air providing from an external source may be regulated to an adjustable level which can be seen on a gauge 59, and may be adjusted by a regulator knob 58. A water trap 60 may filter the compressed air to provide clean air to the whole system.

In some embodiments of the main unit 2, the main unit 2 may be kept in the other positions on the operator such as arm or back. The main unit 2 may also be kept on the floor or hung on a hook so as to provide better comfort to the operator.

Figure 5:
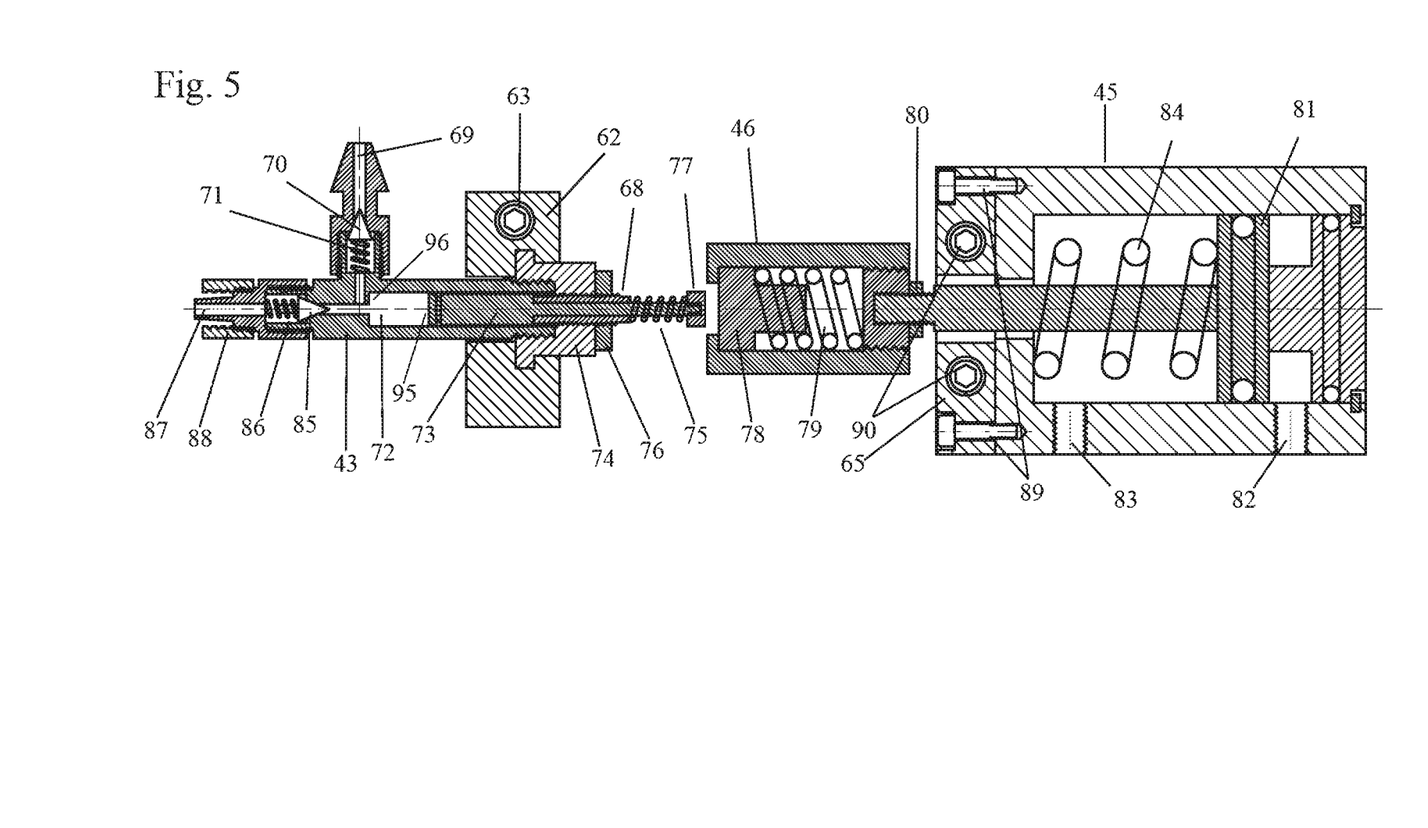
FIG. 5 presents a sectional view of an example of a pumping mechanism on the main unit according to various embodiments described herein.

FIG. 5 provides a closer look at the pumping mechanism by illuminating a sectional view of an example of an actuator 45 and the syringe 43. The actuator 45 may be firmly attached to the panel 67 using a mounting bracket 65. The actuator may be fastened to the bracket 65 by two screws 89 or other suitable connection method, while the bracket 65 may be fastened to the panel 67 with two other screws 90 or other suitable connection method. The syringe 43 may be attached to the panel with the syringe holder 62, fastened to the metal panel by a screw 63 or other suitable connection method. The syringe 43 may be easily detached by loosening the locking screw 64 which can be seen on FIG. 4. When actuated by the compressed air going through the air inlet port 82, the piston 81 will push the shock absorber 46 mounted at the piston 81 rod end with a locking nut 80 toward the syringe 43. The shock absorber 46 hits and pushes the syringe piston 73 until the syringe piston head 95 hit the end of the syringe 96. The movement of the syringe piston 73 pumps the vaccine from the space 72 to the vaccine outlet port 87 through the outlet check valve 85. The vaccine then may be pushed to the finger-held unit 3 via vaccine tube 21 which may be firmly connected to the syringe using a Luer lock 88. The direction of the inlet check valve 70 prevents the vaccine being pumped out to the vaccine inlet port 69. While the actuator piston 81 is still pressed by the compressed air, the shock absorber head 78 presses a stopped syringe piston nut 77 and thus presses an absorber spring 79 until the actuator piston moves 81 to the end. A shock absorber 46 absorbs the stroke force from the actuator 45 and compensates any difference between actuator 45 piston stroke length and the syringe piston 73 stroke length. The absorber also allows the syringe piston 73 movement length to be adjusted using a stroke locking screw 68, means that the syringe 43 can be calibrated for an accurate dosing. When the locking nut 76 is loosened, the stroke locking screw 68 can be adjusted by rotating it until the piston head 95 reaches the desired position and then it can be locked by fastening the nut 76. The changing length of the syringe piston 73 movement allows the empty space 72 volume to be changed, and thus changes the dosing of the injection.

When the actuator piston 81 reaches the end position of the actuator 45, the position detector 47 which can be seen on FIG. 4 may send an electric signal to the controller 49 via detector wire 48. The controller 49 may deactivate the needle actuator solenoid 18, and allow the needle 8 to be withdrawn from of the chicken breast 91. The controller 49 may also stop the electric current to the syringe solenoid valve 54, the compressed air inside the actuator 45 may be exhausted to the syringe solenoid valve 54, which allows the actuator piston 81 to be pushed back to the normal position by the actuator spring 84. The pushed back actuator piston 81 may pull the shock absorber backward and allows the syringe spring 75 to retract the syringe piston 73 to the normal position, causing a negative pressure inside the syringe space 72. The vaccine from the reservoir 5 may be drawn through the vaccine tube 44 and the check valve 70 to fill the empty space 72. The direction of the outlet check valve 85 prevents the vaccine to be drawn back from the vaccine tube 21. The two springs 71 86 of the check valves keep the valves in closed state until a pressure pushes the valves at the right direction. The withdrawal of the needle actuator 30 and syringe actuator 45 settles the whole system to a normal state waiting for a valid actuation signal from push-buttons 11 12 to start another injection.

As mentioned above, when a Bowden cable is used in a further embodiment, the toward movement of the syringe actuator piston 81 releases the tensed core of the Bowden cable serially connects to the syringe actuator piston 81, causing a movement of the needle 8 in the finger-held unit 3 to inject to the chicken breast 91. When the piston 81 is pulled back after the vaccine pumping is done, the actuator piston 81 may also pull the Bowden cable core to pull the needle 8 out of the chicken breast 91.

In other embodiments, when the compressed air actuator 30 is replaced to free the system from the external compressed air source, an electric actuator may be used to push the syringe 43 to pump the vaccine to the finger-held unit 3. With an encoder to determine the length of the movement of the actuator, the dosing of the injection may be firmware determined so that the syringe 43 doesn't need to be calibrated mechanically.

To provide a friendly interface for the operator, the controller 49 may comprise a liquid crystal, light emitting diode (LED), touch screen, or other type of display 50 to display the numbers such as counting number of vaccinated chickens, options to select and messages to prompt or warn the operator. One or more buttons 51 on the controller 49 may allow the operator to provide parameters and control the controller 49.

Figure 6:
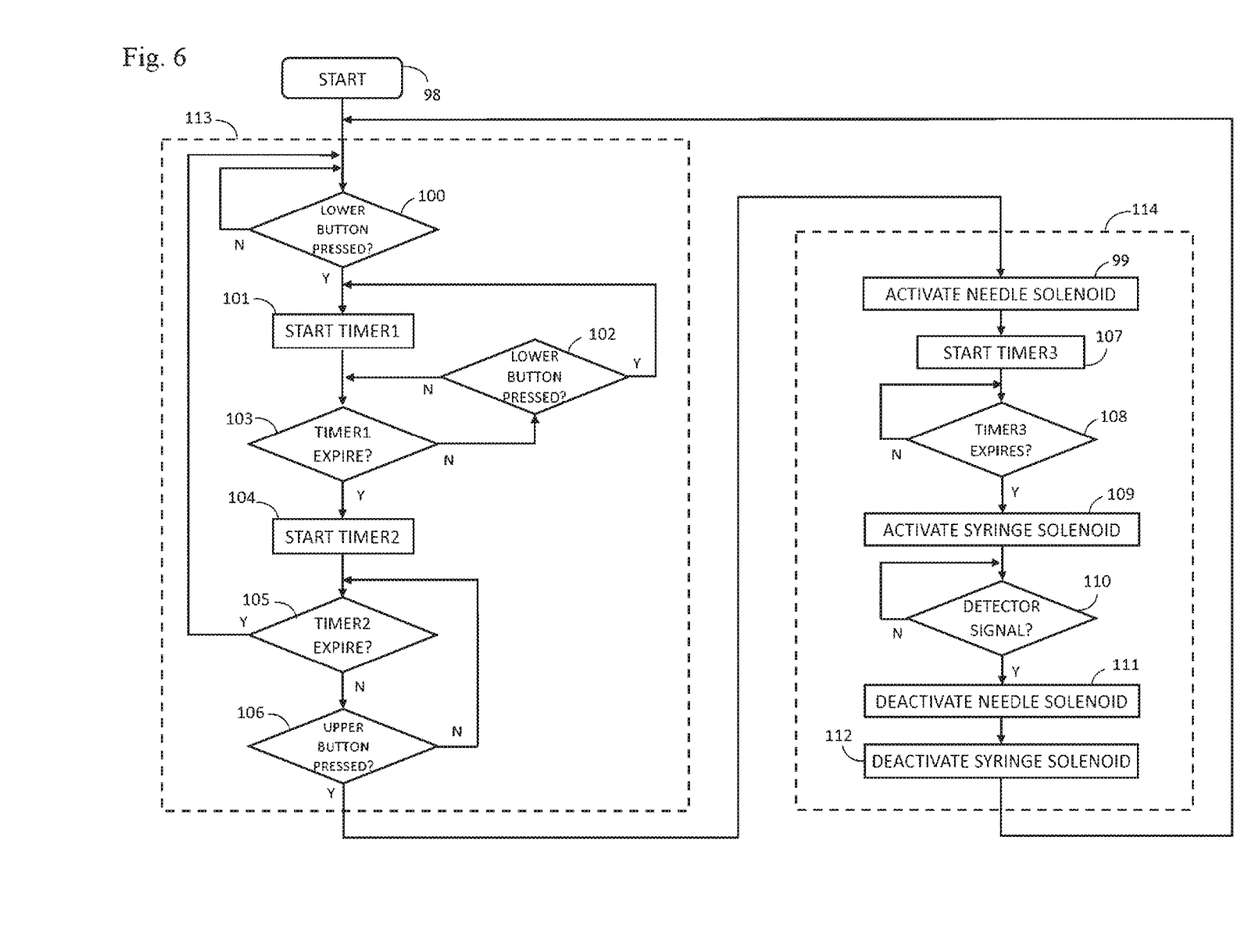
FIG. 6 presents a simplified algorithm flowchart of an example firmware program that may control the device. The flowchart describes a filter algorithm to filter the invalid signals from pushbuttons in finger-held unit to prevent unwanted injections. The flowchart also describes an example of an injection process when it is activated.

FIG. 6 illustrates an example of a simplified algorithm flowchart of a program of a firmware programmable microcontroller on the controller 49. In some embodiments, the program may perform two main routines: filter the signals 113 from push-buttons 11 12 and control an injection 114. When powered, the microcontroller may run the startup process 98 to initiate parameters preparing for the main loop. Then the microcontroller may repeatedly scan 100 the closed-circuit signal of the lower pushbutton 12. When a signal is received, the microcontroller may start a countdown timer 101 and may do nothing until the timer to expire 103. In further embodiments, during the counting down of the timer 103, if the lower push-button is pressed again, the delay time may be reset again 101. The routine may continue until the timer expires without any signal from lower push-button detected, the microcontroller starts another timer 104. During the counting down 105 of the timer, if a signal from the upper push-button 11 is detected, the microcontroller may run the injection routine, if no signal received during the counting down 105 of the timer, it may return to scan 100 the lower push-button 12 signal again. This routine allows the operator to activate an injection by only one way: press the lower push-button, wait a moment predetermined by Timer 1, then press the upper push-button to complete the activation. The routine not only secures the operator from unwanted activation when he inadvertently presses any or both buttons, but also provides another chance to cancel the activation if the selected injection site is not appropriate. A firmware programmable microcontroller on the controller 49 may be reprogrammed with future updates of the program to provide not only safer operation but also more convenience or options for the operator to activate the injections.

When a valid activation is detected, the microcontroller may start the injection routine 114 by activating the needle solenoid 18 to start a process to inject the needle 8 into the chicken's breast. It also may start a timer 107 and countdown 108 until the timer expires. The period set to the timer 107 may be the average value of the period of which starts when the solenoid is activated and ends the moment the needle 8 completely stops, which can be measured in practice. The microcontroller may then activate the syringe solenoid valve 54 to provide compressed air to the actuator 45 to pump the vaccine from the syringe 43 to the needle 8. The microcontroller may then repeatedly check 110 for the signal from the position detector 47 until a signal found, which may signal that a full dose of the vaccine is already pumped to the chicken breast 91. The microcontroller may then stop providing electric currents to the solenoids 18 54 to pull the needle 8 out of the chicken breast 91 and leave the syringe piston 73 moving back to a normal position, thus filling a full dose of vaccine in the syringe 43. The program then return back to the normal status and repeatedly check 101 for the signal from lower push-button 12.

REFERENCES (INCORPORATED HEREIN BY REFERENCE)

U.S. Pat. No. 6,032,612 A to Williams
U.S. Pat. No. 3,964,481 to Gourlandt et al.
U.S. Pat. No. 4,758,227 to Lancaster Jr. et al.
U.S. Pat. No. 8,211,058 to Jorna et al.
U.S. Pat. No. 6,858,020 B2 to Rusnak

The invention claimed is:

1. A portable injector device comprising:
a chassis configured to fit onto at least one of a user's fingers;
an injection unit mounted on said chassis, wherein said injection unit comprises a needle assembly and an actuator,
wherein said actuator is configured to move said needle assembly relative to said chassis from a pre-actuated position to an actuated position, and
wherein an orientation and a position of said needle assembly relative to said chassis is adjustable in said pre-actuated position,
wherein said chassis is U-shaped with two arms, and a needle of said needle assembly is movable between said two arms.

2. The portable injector device of claim 1, wherein said chassis has two slots on each side of said chassis, each slot being configured to receive a user's finger.

3. The portable injector device of claim 2, wherein each slot has an elastic bracket made of a flexible material.

4. The portable injector device of claim 1, further comprising at least one sensor on said chassis, said at least one sensor being configured to generate an injection signal for controlling said actuator when said at least one sensor is activated.

5. The portable injector device of claim 4, wherein said at least one sensor comprises two push-buttons located on an outside face of said chassis and configured to be activated when pushed.

6. The portable injector device of claim 4, further comprising a remote unit comprising a reservoir for a veterinary product.

7. The portable injector device of claim 1, further comprising an adjustment and locking mechanism for adjusting and locking said orientation and said position of said needle assembly relative to said chassis in said pre-actuated position.

8. The portable injector device of claim 7, wherein said adjustment and locking mechanism comprises at least one joint and a screw on said actuator for adjusting and locking said orientation of said needle assembly relative to said chassis in said pre-actuated position.

9. The portable injector device of claim 7, wherein said adjustment and locking mechanism comprises a nut on said actuator for adjusting and locking said position of said needle assembly relative to said chassis in said pre-actuated position.

* * * * *